United States Patent
Womack (10) Patent No.: US 10,551,169 B1
(45) Date of Patent: Feb. 4, 2020

(54) POSITIONING SYSTEM FOR MATERIALS TESTING

(71) Applicant: Epsilon Technology Corporation, Jackson, WY (US)

(72) Inventor: Wesley J. Womack, Jackson, WY (US)

(73) Assignee: Epsilon Technology Corporation, Jackson, WY (US)

( * ) Notice: Subject to any disclaimer, the term of this patent is extended or adjusted under 35 U.S.C. 154(b) by 0 days.

(21) Appl. No.: 15/964,414

(22) Filed: Apr. 27, 2018

(51) Int. Cl.
*G01B 11/16* (2006.01)
*G01N 3/62* (2006.01)
*G01N 3/06* (2006.01)

(52) U.S. Cl.
CPC .......... *G01B 11/167* (2013.01); *G01N 3/068* (2013.01); *G01N 3/62* (2013.01); *G01N 2203/0206* (2013.01)

(58) Field of Classification Search
CPC ...... G02B 26/10; G02B 26/08; G02B 26/105; G02B 27/30; G02B 3/0056; G02B 3/0068; G02B 2027/0112; G02B 26/0808; G02B 26/101; G02B 26/121; G02B 27/0172; G02B 27/0905; G02B 27/425; G02B 27/4272; G02B 5/0268; G02B 5/18; G02B 5/1861; G02B 5/1866; G02B 6/0031; G02B 6/0073; G02B 6/0076; G02B 6/0083; G02B 6/02042; G02B 6/3851; G02B 6/3885; G02B 6/4471; G02B 6/4472; G02B 6/4475; G01B 11/272; G01B 11/25; G01B 11/27; G01B 2210/56; G01B 7/12; G01J 1/0266; G01J 3/0208; G01J 3/0229; G01J 3/0237; G01J 3/0289; G01J 3/2823; G01J 3/36; G01N 21/4788; G01N 21/9501; G01N 21/95607; G01N 2203/0019; G01N 2203/0206; G01N 2203/0405; G01N 3/42; G01N 3/62

See application file for complete search history.

(56) References Cited

U.S. PATENT DOCUMENTS 6,628,978 B1 * 9/2003 Kondo ................ A61B 5/0064
324/248
7,047,819 B2 5/2006 Hayford et al.
7,610,815 B2 11/2009 Hayford et al.
(Continued)

OTHER PUBLICATIONS

"Instron AVE 2 Non-Contacting Video Extensometer" Datasheet. Illinois Tool Works Inc. 2015; 3 pages.
(Continued)

*Primary Examiner* — Michael P Stafira
(74) *Attorney, Agent, or Firm* — Mueting, Raasch & Gebhardt, P.A.

(57) ABSTRACT

Positioning systems adapted to allow repeatable positioning of a test specimen within a test frame, and/or positioning of a sensor (e.g., an extensometer) relative to the specimen. In some embodiments, the positioning system includes two lasers (or other pattern illumination sources) attached to a head, each laser adapted to illuminate a line or other pattern on a face of the test specimen. The two lasers may be configured such that, once the head is at a calibrated working distance from the test specimen, the two patterns intersect one another in a predetermined geometry (e.g., the two lines align (become collinear) with one another).

27 Claims, 10 Drawing Sheets

(56) References Cited

U.S. PATENT DOCUMENTS

| | | | | |
|---|---|---|---|---|
| 2009/0041201 A1* | 2/2009 | Wang | .............. | A61B 6/08 |
| | | | | 378/206 |
| 2013/0155416 A1* | 6/2013 | Umemura | .......... | G01B 11/2509 |
| | | | | 356/610 |
| 2014/0267702 A1* | 9/2014 | Profitt | ................. | G01B 11/022 |
| | | | | 348/136 |
| 2016/0016317 A1* | 1/2016 | Trompeter | ............. | B25J 9/1692 |
| | | | | 700/254 |
| 2016/0074003 A1* | 3/2016 | Manke | .................... | A61B 6/08 |
| 2016/0184994 A1* | 6/2016 | Trompeter | ............. | B25J 9/1692 |
| | | | | 700/254 |

OTHER PUBLICATIONS

"DW0822 Self-Leveling Cross Line/Plumb Spot Combination Laser" Instruction Manual, DeWALT Industrial Tool Co., 2013; 6 pages.

"Handheld for 'Point and Shoot' Deformation & Strain Measurements—Digital 3D Image Correlation System Q-480" Datasheet. Dantec Dynamics. Believed available at least as early as Dec. 13, 2017; 2 pages.

"Q-480 Handheld DIC for Displacement & Strain Measurement" Datasheet. Dantec Dynamics. Publ. No. PI-Q-480_RWD. Believed available at least as early as Dec. 13, 2017; 2 pages.

"CMOS/CCD Line Scan Sensors ZS64A5K and ZS16A(HS)." Website. H.-D. Rudolph GmbH. [retrieved on Dec. 15, 2018]. Retrieved from the Internet:<URL:https://www.rudolph-optik.de/en/basic-products/ccd-line-scan-sensor-zs16a>. Website believed available at least as early as Oct. 9, 2017; 2 pages.

"UVX Extensometer Modules" Datasheet. iMETRUM. Published Jun. 27, 2017; 3 pages.

* cited by examiner

POSITIONING SYSTEM FOR MATERIALS TESTING

The present disclosure is directed generally to materials testing equipment and, more particularly, to positioning systems for positioning a non-contact extensometer or other component relative to a test specimen, and/or for positioning a test specimen within a test frame.

BACKGROUND

Various devices are known for measuring displacement or strain. For instance, in materials testing, devices known as extensometers are frequently used to measure strain (defined as a change in length ($\Delta L$) over original length (L); or $\Delta L/L$) of a test specimen. Although different configurations are known, the term "extensometer" may refer to most any device that incorporates a sensor capable of measuring relatively small increments of deformation of the test specimen.

One type of extensometer is a mechanical or "contact" extensometer. These devices use spaced-apart arms having knife edges or other contact elements at their distal ends. The arms may be joined to one another at or near their proximal ends via a flexible transducer assembly. The knife edges are attached to the test specimen at a preset distance from one another (the "gauge length" of the extensometer). During testing, the knife edges move with the test specimen as the latter deforms. The deformation or strain is then detected and measured, typically with strain gauges contained within the transducer assembly.

While effective, contact extensometers are not well-suited for all testing applications. For instance, extremely fragile materials may present problems for both extensometer attachment and measurement. Moreover, contact extensometers—when used with materials that fail violently—may yield inaccurate readings at or near specimen failure, and, moreover, may be damaged by the failing specimen. Still further, contact extensometers require physical attachment to, and detachment from, each test specimen. Such a repetitive procedure may slow throughput when multiple test specimens are sequentially tested.

To address these and other concerns, optical or "non-contact" extensometers are sometimes used. These extensometers may utilize cameras to optically detect deformation by, for example, monitoring marks on the specimen from a remote, non-contacting location.

While effective, non-contact extensometers are prone to various issues. For instance, with non-contact extensometers, it is often difficult to set a desired working distance from the extensometer sensor to the test specimen in an accurate and repeatable manner. As a result, tedious and time-consuming setup and adjustment may be required with each test specimen.

SUMMARY

Embodiments described herein may provide a positioning system for use with locating components within a materials test frame, wherein the system includes: a base positionable relative to the test frame; and a head connected to the base and movable toward and away from a test specimen secured within the test frame. A first pattern illuminator is connected to the head and adapted to illuminate a visible first pattern on the test specimen, while a second pattern illuminator is connected to the head and adapted to illuminate a visible second pattern on the test specimen. The first and second patterns intersect one another in a predetermined geometry when the head is located at a calibrated working distance from the test specimen, and do not intersect one another in the predetermined geometry when the head is at a distance different than the calibrated working distance.

In another embodiment, a positioning system is provided for locating a non-contact extensometer relative to a test specimen secured within a specimen area, and along a test axis, of a test frame. The system may include: a base adapted to attach to the test frame; a head connected to the base; a first pattern illuminator connected to the head and adapted to illuminate a first pattern obliquely intersecting the test specimen; and a second pattern illuminator connected to the head and adapted to illuminate a second pattern also obliquely intersecting the test specimen. The first and second patterns: intersect one another in a predetermined geometry on a face of the test specimen when the head is located at a calibrated working distance from the test specimen; and do not intersect one another in the predetermined geometry when the head is located at a distance different than the calibrated working distance.

In still another embodiment, a method for positioning a sensor relative to a face of a test specimen is provided. The method includes: aligning the sensor with the test specimen; activating two pattern illuminators associated with the sensor, the two pattern illuminators illuminating two patterns upon the face of the test specimen; and changing a distance between the sensor and the test specimen until the two patterns align on the face of the test specimen in a predetermined geometry.

In still yet another embodiment, a positioning system for use with locating a test specimen within a materials test frame is provided. The system includes: a pattern illuminator adapted to be fixed relative to the test frame and adapted to illuminate a visible first line on the test specimen.

The above summary is not intended to describe each embodiment or every implementation. Rather, a more complete understanding of illustrative embodiments will become apparent and appreciated by reference to the following Detailed Description of Exemplary Embodiments and claims in view of the accompanying figures of the drawing.

BRIEF DESCRIPTION OF THE VIEWS OF THE DRAWING

Exemplary embodiments will be further described with reference to the figures of the drawing, wherein:

FIGS. 8A-8D illustrate specimen illumination using the exemplary positioning system of FIGS. 5-7 to illuminate two patterns, each pattern being a vertical laser line or plane, wherein.

FIGS. 9A-9D illustrate scenarios in which positioning systems in accordance with embodiments of the present disclosure are used to align a test specimen relative to a test axis, wherein.

FIGS. 10A-10B illustrate alternative specimen illumination patterns wherein one pattern is a vertical line or plane and the other pattern is formed by two intersecting lines or planes (e.g., an "X" shaped pattern), wherein.

FIGS. 11A-11B illustrate other illumination patterns wherein one pattern is a vertical line or plane and the other pattern is formed by two intersecting lines or planes (e.g., a cross or "+" shaped pattern), wherein.

FIGS. 12A-12B illustrate yet other illumination patterns wherein one pattern is a line or plane and the other pattern is formed by a series of parallel lines, wherein: FIGS. 13A-13B illustrate still other illumination patterns wherein one pattern is a line or plane and the other pattern is a point or circle, wherein.

The figures are rendered primarily for clarity and, as a result, are not necessarily drawn to scale. Moreover, various structure/components, including but not limited to fasteners, electrical components (wiring, cables, etc.), and the like, may be shown diagrammatically or removed from some or all of the views to better illustrate aspects of the depicted embodiments, or where inclusion of such structure/components is not necessary to an understanding of the various exemplary embodiments described herein. The lack of illustration/description of such structure/components in a particular figure is, however, not to be interpreted as limiting the scope of the various embodiments in any way. Still further, the terms "Figure x" and "FIG. x" may be used interchangeably herein.

DETAILED DESCRIPTION OF EXEMPLARY EMBODIMENTS

In the following detailed description of illustrative embodiments, reference is made to the accompanying figures of the drawing which form a part hereof. It is to be understood that other embodiments, which may not be described and/or illustrated herein, are certainly contemplated.

Embodiments of the present disclosure are directed to positioning systems for use with materials testing equipment such as tensile, compressive, and fatigue testing machines. For instance, in some embodiments, such positioning systems may be associated with a non-contact (e.g., optical) extensometer to permit accurate and repeatable positioning of the extensometer relative to a test specimen located within a test frame. In other embodiments, positioning systems in accordance with embodiments of the present disclosure may be used to align a component, e.g., the test specimen itself, relative to a test axis of the test frame. Regardless of the particular application, positioning systems like those described herein may provide benefits over other known positioning systems by allowing simple and accurate positioning in a cost-effective manner.

All headings provided herein are for the convenience of the reader and should not be used to limit the meaning of any text that follows the heading, unless so specified. Moreover, unless otherwise indicated, all numbers expressing quantities, and all terms expressing direction/orientation (e.g., vertical, horizontal, parallel, perpendicular, etc.) in the specification and claims are to be understood as being modified in all instances by the term "about." Still further, the term "and/or" (if used) means one or all of the listed elements or a combination of any two or more of the listed elements. "I.e." is used as an abbreviation for id est, and means "that is." "E.g.," is used as an abbreviation for exempli gratia, and means "for example."

It is noted that the terms "comprises" and variations thereof do not have a limiting meaning where these terms appear in the accompanying description and claims. Further, "a," "an," "the," "at least one," and "one or more" are used interchangeably herein. Moreover, relative terms such as "left," "right," "front," "fore," "forward," "rear," "aft," "rearward," "top," "bottom," "side," "upper," "lower," "above," "below," "horizontal," "perpendicular," "vertical," and the like may be used herein and, if so, are from the perspective indicated in the particular figure. These terms are used only to simplify the description, however, and not to limit the interpretation of any embodiment described.

Figure 1:
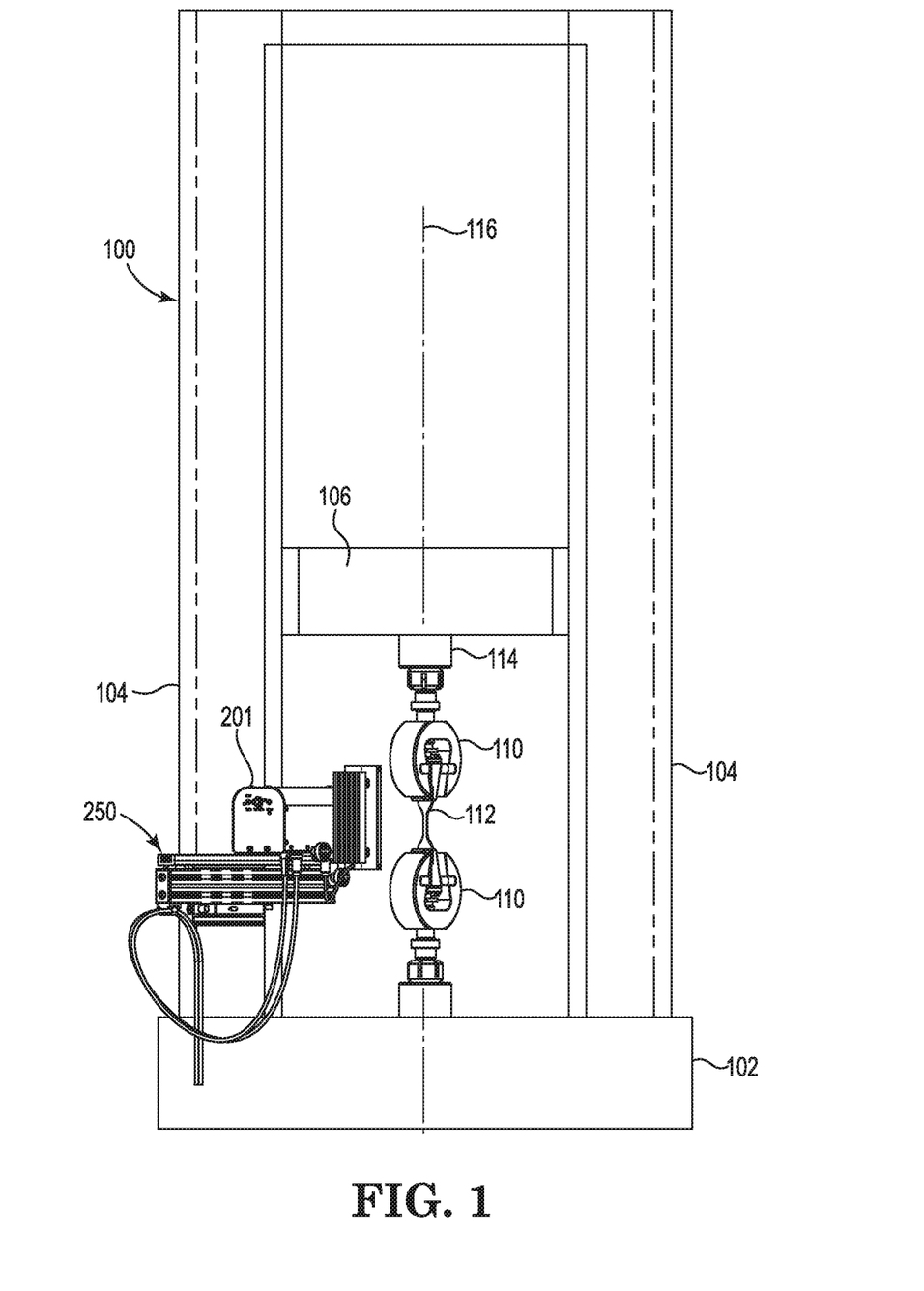
FIG. 1 illustrates a test frame and a non-contact extensometer, wherein the extensometer is illustrated with a positioning system in accordance with embodiments of the present disclosure, the positioning system adapted for setting a distance from a sensor of the extensometer to a test specimen, and/or indicating or detecting alignment of the specimen within the test frame.
Figure 2:
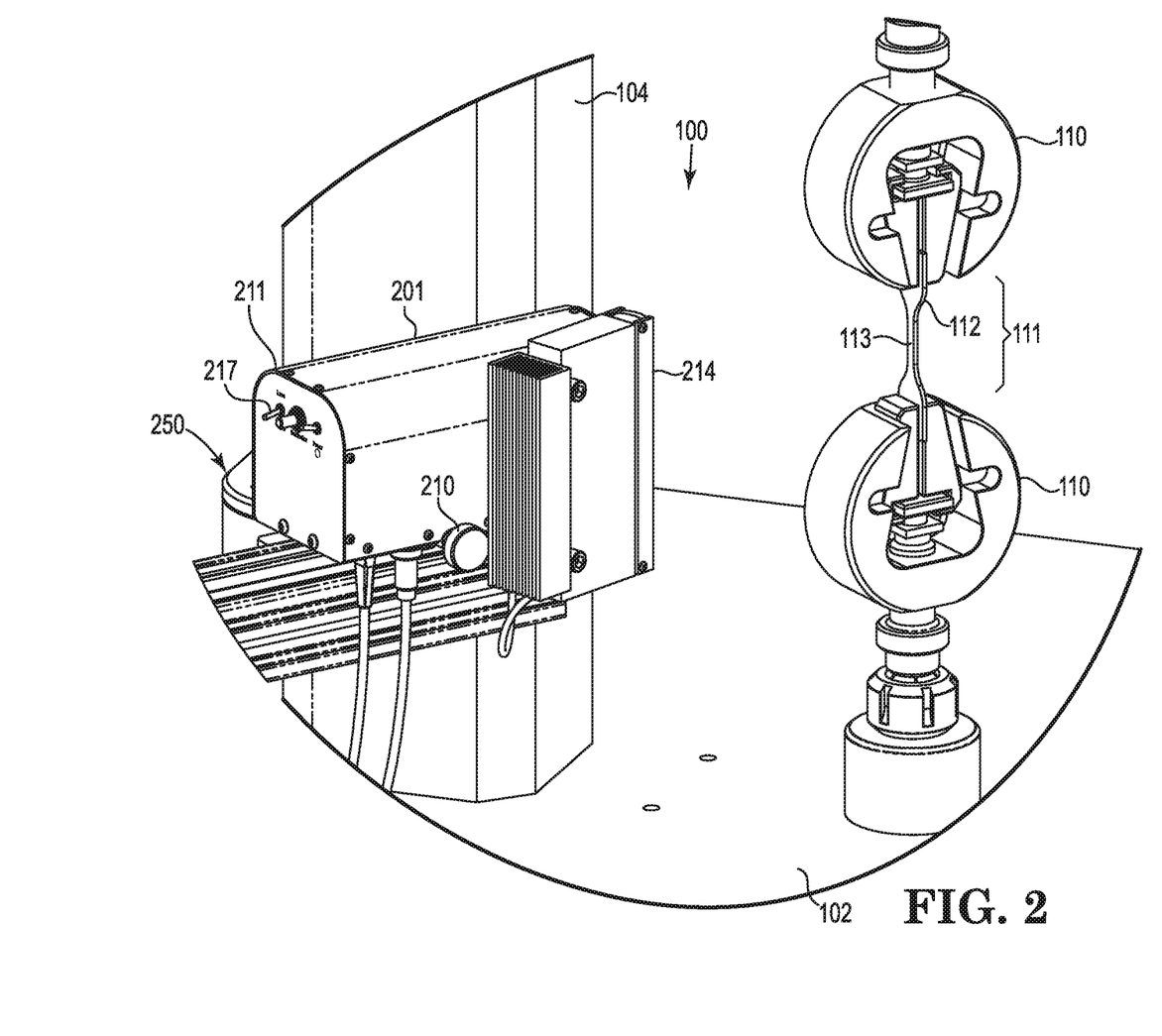
FIG. 2 is an enlarged perspective view of the extensometer and positioning system of FIG. 1.

With reference to the figures of the drawing, wherein like reference numerals designate like parts and assemblies throughout the several views, FIGS. 1 and 2 illustrate an exemplary materials test frame 100. The frame 100 may include a base plate 102, vertical columns 104 fixed to the base plate, and a crosshead 106 that may be movably supported along the columns, e.g., via actuators (e.g., screws, not shown) attached to or contained within the columns. A specimen grip 110 may be attached to the base plate 102, while another specimen grip 110 may be supported by the crosshead 106. A test specimen 112 may be held by the grips 110 during testing in a test area 111 defined generally as the area between the two grips. The components of the test frame 100 (e.g., the grips 110) may be aligned with one another along a common or test axis 116 that represents a true axis of tension and compression of the test frame 100.

By controlling movement of the crosshead 106, various loads (e.g., tensile, compressive) may be applied directly to the test specimen 112. For example, the crosshead 106 may move under displacement control (e.g., using a linear variable differential transformer or LVDT or encoders (not shown) associated with the screws that move the crosshead 106 as the displacement sensor) or under load control (e.g., using a load cell 114 associated with either the upper grip 110 (as shown) or the lower grip as the load sensor). Load and displacement data (e.g., from the load cell and encoders, respectively) may be captured by an electronic data collection unit (not shown) and, optionally, used as feedback in a closed loop controller (also not shown) to control the actuator as is known in the art.

While illustrated as a screw-driven test machine, such a configuration is not limiting. For example, the base plate 102 may support a linear hydraulic actuator connected directly to the lower grip 110 that may apply various loads to the test specimen. In such a configuration, the crosshead 106 may be movable to different locations along the columns 104, but then fixed during actual testing.

In certain applications, measurement of specimen elongation may require accuracy greater than that provided by the actuator's onboard displacement sensor (e.g., the LVDT or encoders). In such instances, an extensometer may be used. While various contact extensometers are available, some test specimens (e.g., fragile specimens or those that may fail violently) are better suited to strain measurement using non-contact extensometers. Although positioning systems in accordance with embodiments of the present disclosure may find use in non-extensometer applications as further described below (e.g., to locate specimens properly within grips of the test frame as described in reference to FIGS. 9A-9D), FIGS. 1-8D illustrate positioning systems configured for use in conjunction with non-contact extensometers to accurately and repeatably locate the extensometer relative to the test specimen.

Figure 3:
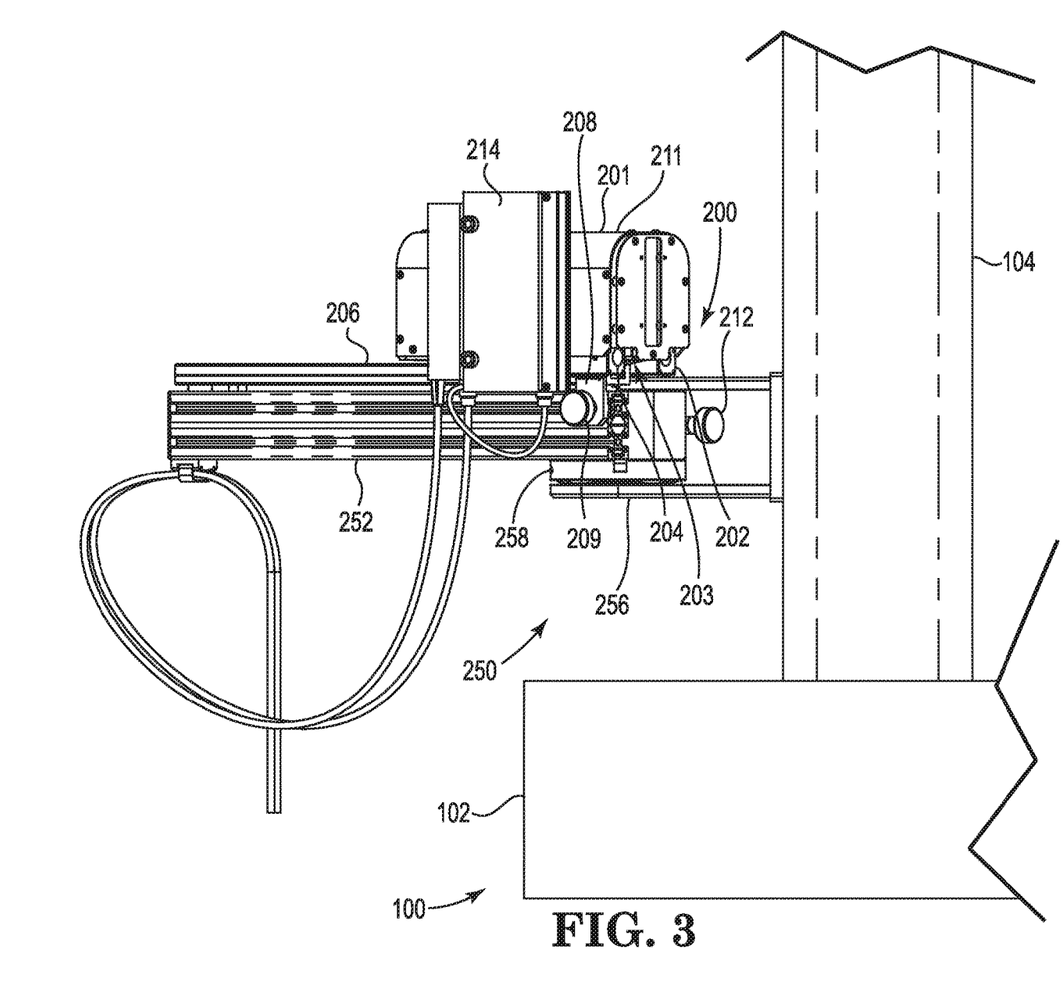
FIG. 3 is a side elevation view of the extensometer and positioning system of FIG. 1.
Figure 4:
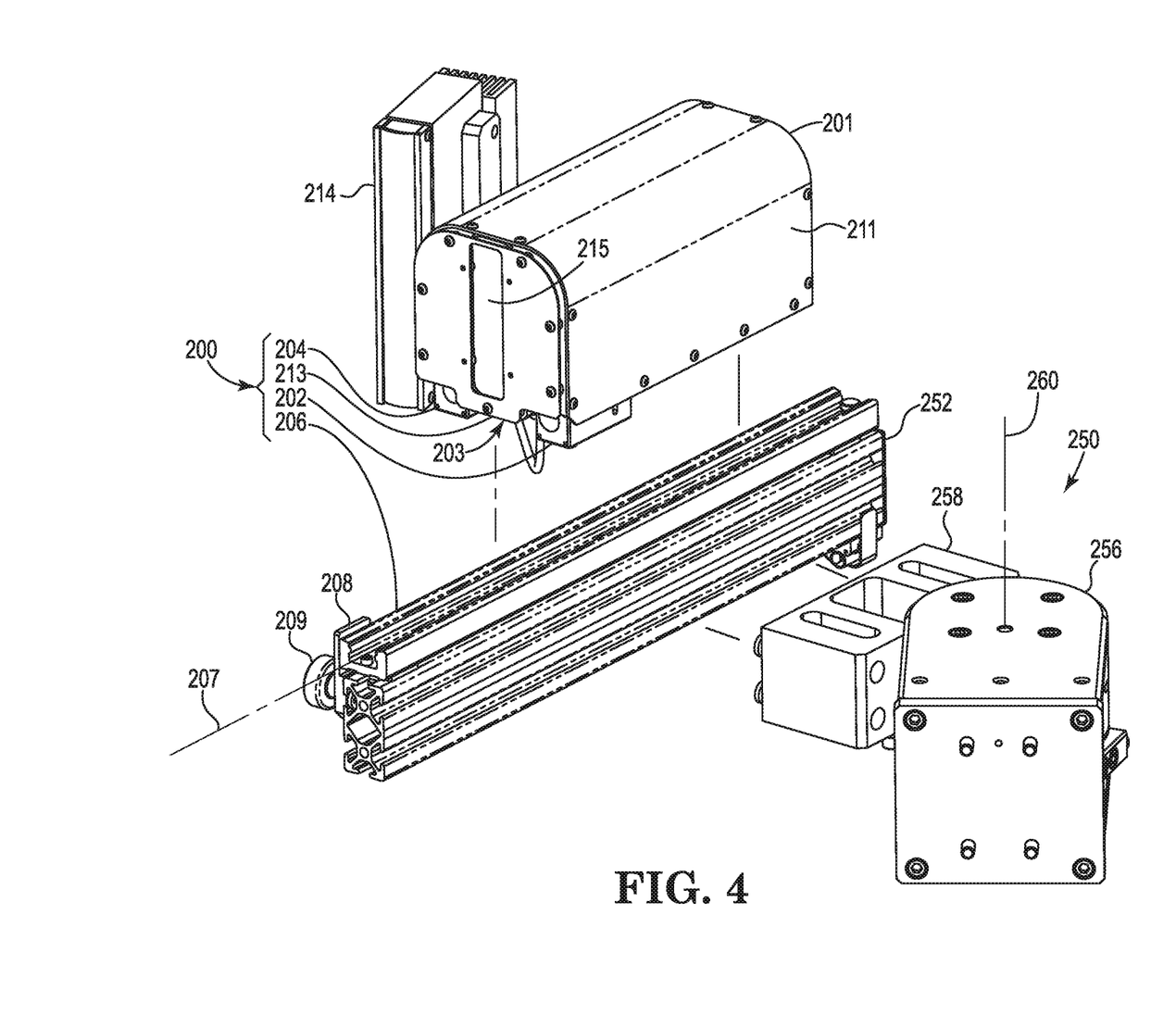
FIG. 4 is an exploded view of the extensometer and positioning system of FIG. 1.

With initial reference to FIGS. 3-4, a positioning system 200 in accordance with embodiments of the present disclosure is illustrated. The exemplary positioning system 200 may include two (or more) pattern illumination sources or "illuminators." In the illustrated embodiments, the pattern illuminators are configured as lasers, e.g., first laser 202 and second laser 204 (although other pattern illuminators (e.g., spotlights) may also be used), connected to a head 203. As described below, the head 203 may also support a sensor, e.g., extensometer 201. The positioning system 200 may further include a base 250 having an arm 252 that supporting a linear slide or bearing 206 in relation to the test frame 100. The base 250 may optionally include, in addition to the arm 252, a mount 256 secured to one of the frame columns 104 (or to the base plate 102), and a support 258 pivotally attached to the mount such that the support may pivot, relative to the mount, about a pivot axis 260.

Of course, while shown as utilizing an articulating base 250, such a configuration is exemplary only as other bases (e.g., those lacking articulation, or those including more than one articulating joint) are certainly possible without departing from the scope of this disclosure. For example, alternative positioning systems may be adapted only for moving the head 203 toward or away from the specimen, while still others may be fixed relative to the test frame. Fixed illuminators may be useful, for example, to assist with specimen alignment and positioning as further described below.

Accordingly, in a broad sense, positioning systems in accordance with embodiments of the present disclosure may include two or more illuminators that are positionable (or fixed) in relation to a test plane (e.g., a face 113 of the test specimen 112; see FIG. 2). While the illuminators are described herein as both being connected to a common head 203, such a configuration is not limiting as, for example, fixed-type illuminators could be independently mounted on the test frame (e.g., on opposite columns) without departing from the scope of this disclosure. Regardless of how the illuminators are mounted (fixed or movable), however, positioning systems like those described herein allow accurate and repeatable positioning of one component (e.g., a test specimen) relative to another component (e.g., to the test frame 100, or to the head 203).

In the illustrated embodiments, the exemplary base 250 is adapted to attach and support the positioning system 200 (and, where included, the extensometer 201/head 203) relative to the frame 100, and further allow positioning and reorientation of the head 203 relative to the test specimen. For instance, with the articulating base 250 illustrated in the figures, the base allows pivotal movement of the support 258/arm 252/bearing 206 about the pivot axis 260, thereby allowing positioning and angular reorientation of the linear bearing relative to the face 113 of the test specimen 112 (see FIG. 2).

Figure 7:
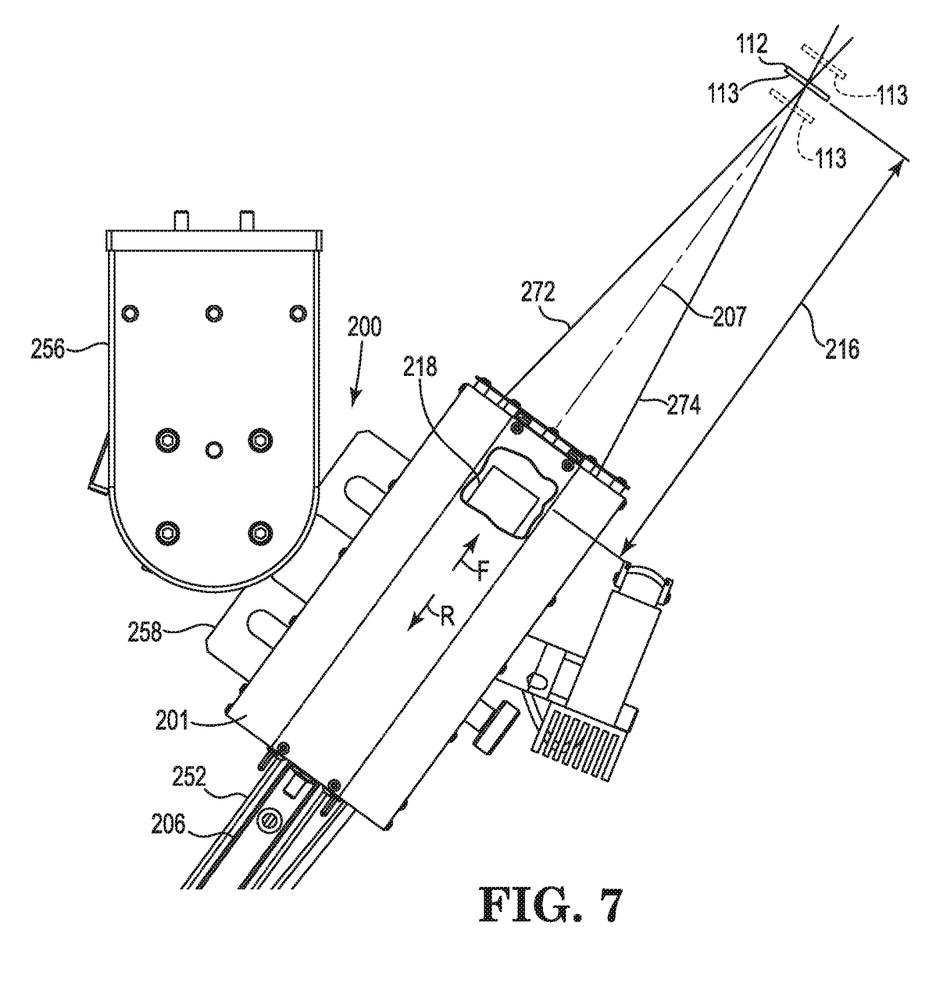
FIG. 7 is a top plan view of the positioning system of FIG. 6.

As stated above, the lasers 202, 204 may form or be connected to the unitary head 203 (see exploded view of FIG. 4), the latter of which may also include a sensor (see, e.g., sensor portion 218 of the extensometer shown in cut-away in FIG. 7). For example, the unitary head 203 may incorporate an upper slide 213 (see FIG. 5) that forms the lower surface of the head, i.e., the upper slide 213 may form a platform upon which the various components of the head 203 (e.g., lasers 202, 204, extensometer 201, etc.) may be attached and supported. As is known in the art, the upper slide 213/head 203 may translate along and relative to the bearing 206 (wherein the bearing is formed by, or affixed to, an upper surface of the arm 252 itself) along a bearing axis 207 (see FIG. 4), wherein the bearing axis 207 may be oriented in a direction perpendicular to the test axis 116 (see FIG. 1). Stated another way, the head 203 is movable (relative to the base 250 itself) toward and away from the face 113/test axis 116. In some embodiments, this movement is accommodated by translation of the head 203 toward and away from the test specimen 112 or at least toward and away from the face 113/test axis 116.

Figure 5:
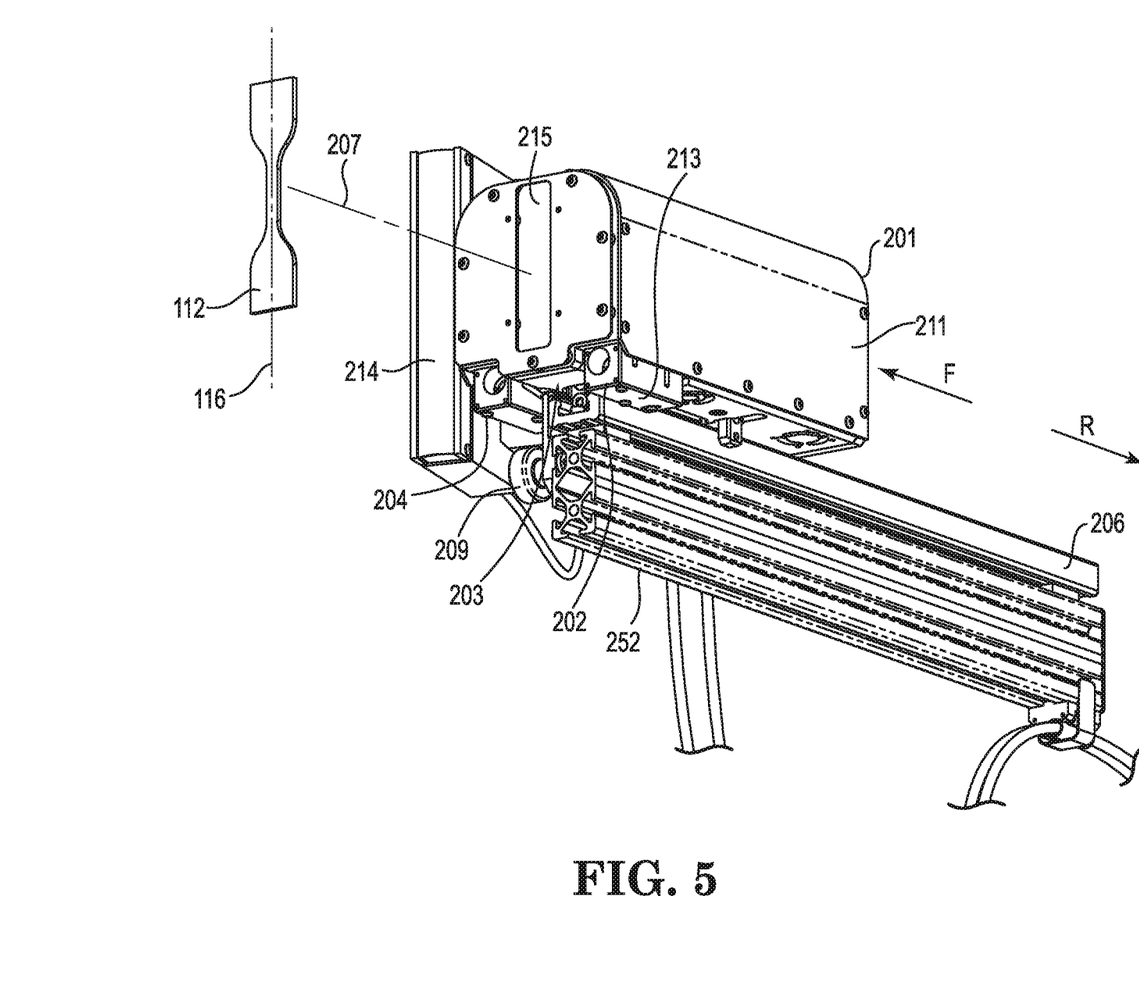
FIG. 5 is an isolated and enlarged perspective view of a positioning system and extensometer in accordance with embodiments of the present disclosure.

The bearing 206 and/or the arm 252 may further include various features that assist in fixing a position of the head 203 along the arm. For example, the arm 252 (or the bearing 206) may include a stop 208 as shown in FIG. 4. The stop 208 may include a thumb wheel 209 that may be loosened to permit the stop to be relocated along the arm 252/bearing 206. Once the thumbwheel 209 is re-tightened, the stop may be immobilized in place along the bearing 206. As one can appreciate, the stop 208 forms an adjustable abutting surface or hard stop that limits forward (i.e., "forward" and "F" as used in this context means toward the specimen face 113/test axis 116 as shown in FIG. 5, while "rearward" or "R" means away from the specimen face/test axis) placement of the head 203 along the bearing 206.

A head lock may also be included as shown in FIG. 2. The head lock may be configured as a thumbwheel 210 that threadably engages the head and may be tightened until it contacts the bearing 206. As a result, the thumbwheel 210 may be loosened to permit the head 203 to slide along the bearing 206 toward (forwardly) and away (rearwardly) from the specimen 112. Once the head 203 reaches the desired position as determined by the positioning system 200 (as further described below), however, the thumbwheel 210 may be rotated (tightened) to lock the head in position relative to the arm 252/bearing 206. The base 250 may include a similar stop (see, e.g., stop 212 in FIG. 3) and lock (not shown) for limiting and ultimately locking pivotal movement of the support 258 relative to the mount 256.

The head 203 may support other components beneficial to use of the positioning system and/or the extensometer. For example, in the embodiment illustrated in FIGS. 1-4, the head 203 may also support a diffuse illumination source (e.g., a diffuse illuminator 214) for use during testing (e.g., to illuminate gauge marks (not shown) or other patterns or features on the test specimen 112). Various electrical components, wires, controls, etc. may also be supported by the head 203 as needed.

As described above, embodiments of the base 250 may include the articulating arm and bearing. However, such a configuration is exemplary only as embodiments that lack such a mounting system, or utilize a different mounting style, are certainly contemplated. For instance, the bearing 206, stop 208, and head lock may be replaced with a micrometer adjustable slide without departing from the scope of this disclosure. Moreover, substituting a pivoting base for the bearing 206 is also contemplated. Finally, in some embodiments the base may be fixed (e.g., to the test frame).

As stated elsewhere herein, the extensometer 201 may be configured as an optical extensometer that, in general, uses a laser or a camera (see sensor portion 218 in FIG. 7) to detect gauge marks or patterns on the face 113 of the test specimen 112 (see FIG. 2). The camera may be contained within a housing 211, wherein a lens of the camera aligns with the test specimen 112 (during testing) through a window 215 formed in the housing (see FIG. 4). In the illustrated embodiment, the lens of the camera is located within the housing 211 and has no remote adjustment features.

Most non-contact extensometers are designed, adjusted, or calibrated for use at a specific working distance (the "calibrated working distance") from the specimen. That is to say, the extensometer 201 benefits from being precisely located relative to the test specimen 112 during testing. If the working distance is incorrect, measurement errors result due to scaling errors and other effects. Accordingly, for each test specimen, the extensometer 201 is first positioned at the calibrated working distance from the face 113 of the test specimen 112. These distance setting procedures are often tedious, yet are needed to ensure proper extensometer placement and/or adjustment relative to the specimen. For example, physical gage blocks may be used. While effective, such blocks are expensive to manufacture and prone to damage and loss. In other non-contact extensometers, ranging may be achieved using sophisticated software metrics (e.g., sharpness, scaling, focus). Again, while effective, such methods are often costly and sometimes tedious to execute.

Such positioning issues may be minimized, or even eliminated, with positioning systems in accordance with embodiments of the present disclosure. While various embodiments are contemplated, the exemplary positioning system 200 may utilize two pattern illuminators or laser light sources (e.g., the lasers 202 and 204) that are each able to illuminate a visible pattern on the face 113 of the test specimen 112. As used herein, "visible" means that the pattern illuminated is detectable by one or more of a human eye and an instrument (e.g., extensometer camera or other machine that may detect wavelengths normally outside the human-visible spectrum e.g., infrared or ultraviolet light) such that the illuminated pattern may be observed. As further described below, when the head 203 is spaced from the face 113 of the specimen at the calibrated working distance, these two illuminated patterns will intersect in a predetermined geometry upon the face. As used herein, "predetermined geometry" is defined as an observable interaction between the two patterns (e.g., crossing of the patterns in a defined manner, alignment of some part of one pattern with some part of the other, etc.) that is readily discernable.

In some embodiments, the illuminated pattern produced by each of the two lasers may be a discrete line (for purposes of this description, the terms "line" and "plane" may be used interchangeably herein). For instance, the patterns may consist of two parallel, vertical lines that will overlay (become collinear with) one another upon the face 113 of the specimen when the head 203 is at the calibrated working distance. However, as described below, other illuminated patterns are also possible. In fact, any structured illumination patterns that may interact in a detectable manner (e.g., may intersect one another in a predetermine geometry) once the head 203 is located at the calibrated working distance are possible without departing from the scope of this disclosure.

As stated above, in the illustrated embodiments the two lasers 202, 204 are attached to the extensometer 201 (e.g., to the head 203) such that their respective illuminated patterns (lines) upon the face 113 of the test specimen intersect when the head is at a distance corresponding to the calibrated working distance of the extensometer. That is to say, the head 203 may be adjusted, e.g., along the bearing 206, until the two laser lines/planes become collinear on the face 113 of the specimen as described below, indicating that the extensometer 201 is at the calibrated working distance from the face of the specimen. At this point, testing may begin. Conversely, when the head 203 is located at a distance different than the predetermined distance, the two lines may appear parallel to, but offset from, one another. That is to say, the two lines will not intersect one another in the predetermined geometry when the head 203/extensometer 201 are not at the calibrated working distance.

Figure 6:
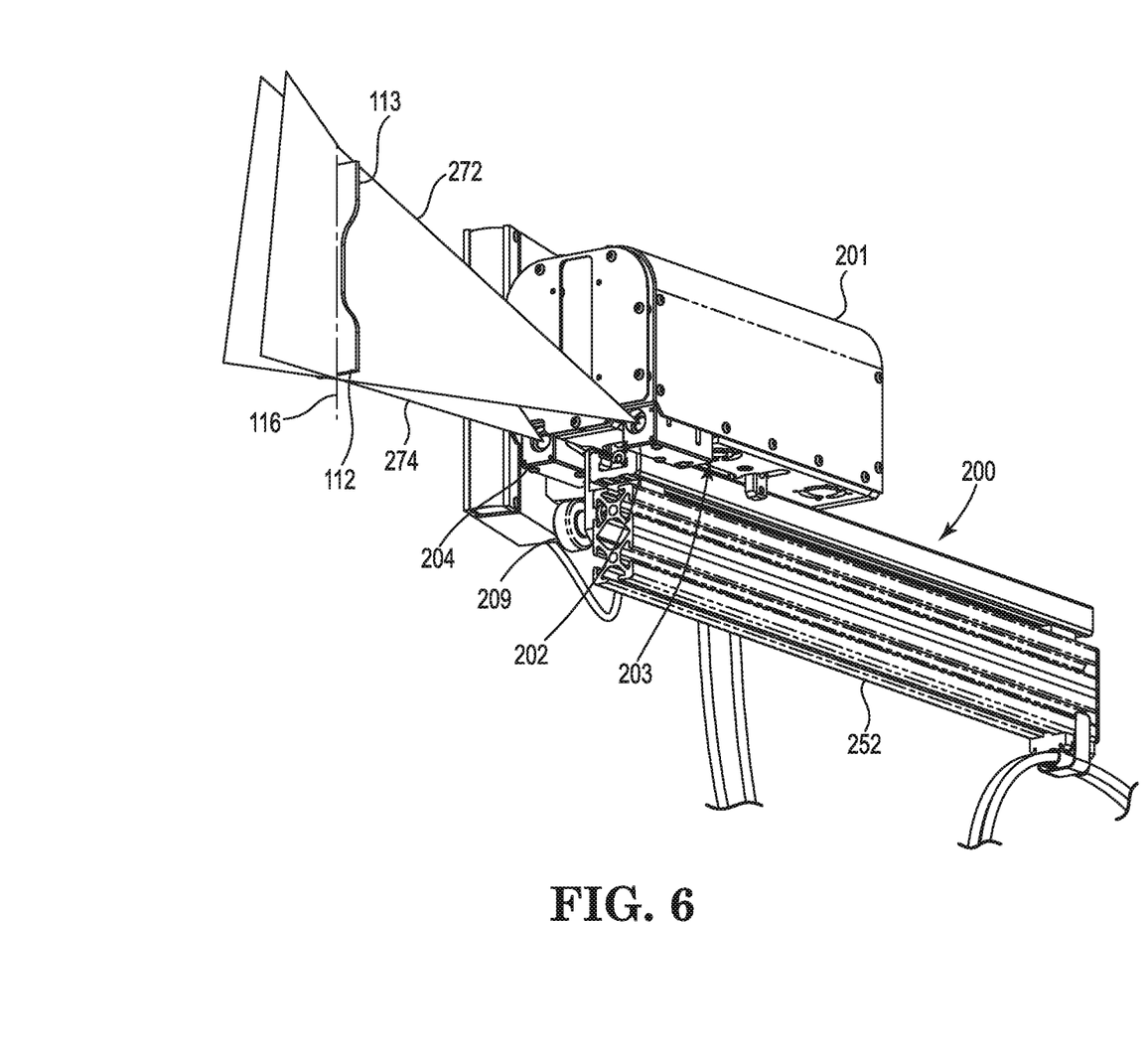
FIG. 6 is a view similar to FIG. 5 illustrating operation of the exemplary positioning system.

FIGS. 5-7 illustrate an exemplary method of using the positioning system 200 to position the extensometer 201 relative to the test specimen 112. As with FIG. 4, aspects of the test frame 100 and specimen grips 110 are not illustrated in FIGS. 5-7.

As an initial matter, the base 250 (only the arm 252 is shown in FIGS. 5-7) may be positioned to ensure the bearing axis 207 aligns with (intersects) the test axis 116. When the base 250 is so positioned, the arm 252 may be locked in place to prevent movement of the arm relative to the mount 256 (see FIG. 3). However, the head 203 may continue to translate along the arm (and relative to the support 258) toward (direction "F" in FIG. 5) and away (direction "R") from the specimen (radially to the test axis) as needed to adjust a distance between the extensometer and the specimen 112. As described above, the translation of the head 203 may be constrained in the forward direction by the adjustable stop 208/thumbwheel 209, and may be selectively immobilized, relative to the arm, by the thumbwheel 210.

With the base 250 angularly oriented to generally align the bearing axis 207 with the test axis 116, the head 203/extensometer 201 may slide rearwardly, i.e., away from the test specimen 112, to provide space for the operator to remove/replace the test specimen 112. Once the specimen is inserted into the grips 110 (see FIG. 2), the head 203/ extensometer 201 may be advanced forwardly (toward the specimen) by first loosening the thumb wheel 210 and sliding the head 203 along the arm 252.

Figure 8A:
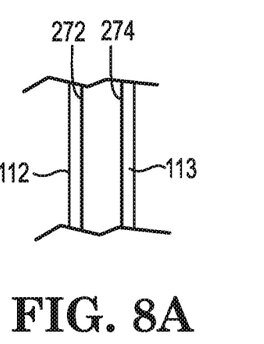
FIG. 8A illustrates the two offset laser lines or planes visible on a face of a test specimen when a distance to the specimen face is more than (or less than) a calibrated working distance.

To determine the proper location of the head 203 along the bearing 206, the positioning system 200 may be utilized. To utilize the positioning system, the lasers 202, 204 may first be energized. In some embodiments, laser illumination may occur manually by actuating a switch 217 (see FIG. 2) on the extensometer housing 211. Once the lasers 202, 204 are energized, laser planes 272, 274, respectively, become visible as indicated in FIG. 6. These planes 272, 274 obliquely intersect the face 113 of the specimen 112, appearing as visible lines as shown in FIG. 8A. In the illustrated embodiments, these lines 272, 274 are parallel to the test axis 116 (e.g., vertical). The head 203 may then be manually moved, forwardly (toward the specimen 112) or rearwardly (away from the specimen) until the lines 272, 274 appear collinear on the face 113 of the specimen 112 as shown by the solid line specimen in FIG. 7 (the two specimen distances shown in broken lines in FIG. 7 illustrate the relative line locations 272, 274 when the head 203 is too close to, or too far from, the specimen).

Once again, while illustrated herein as having a fixed specimen position and a movable head 203, such a configuration is exemplary only. For example, some testing protocols may benefit from a fixed head 203 position and instead rely on setting the calibrated working distance via specimen movement. Such a configuration may be suitable, for example, when testing specimens in compression (using compression platens). When using a fixed head 203, the operator may manipulate the location of the test specimen until the laser patterns indicate the calibrated working distance is set.

Figure 8B:
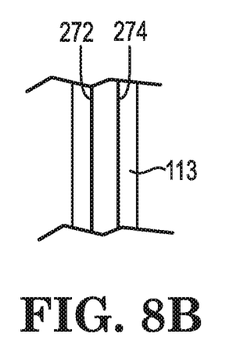
FIG. 8B is a view similar to FIG. 8A, after repositioning of the sensor (or specimen) to a position closer to the calibrated working distance.
Figure 8C:
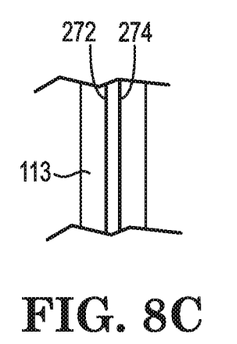
FIG. 8C is a view similar to FIG. 8B, after movement of the sensor (or specimen) to a position even closer to the calibrated working distance.
Figure 8D:
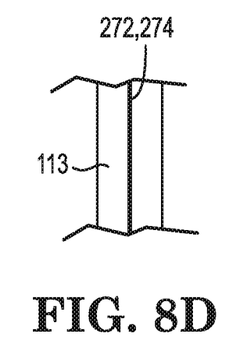
FIG. 8D is a view similar to FIG. 8C after movement of the sensor (or specimen) to a position corresponding to the calibrated working distance, wherein the laser two lines are collinear.

FIGS. 8A-8D illustrate an exemplary method of using the positioning system 200. As shown in FIG. 8A, the lines 272, 274 (resulting from the illuminated planes of the lasers 202, 204) may initially appear to be parallel to, and offset or spaced-apart from, one another on the specimen face 113. The operator may then loosen the thumbwheel 210 (see FIG. 2) and slide the head 203 rearwardly. If the lines 272, 274 move farther apart, for example, the operator may instead move the head 203 forwardly. Once the movement direction (forwardly or rearwardly) of the head 203 needed to set the extensometer 201 position is determined, the operator may continue to advance/withdraw the head manually, wherein the lines 272, 274 will begin to converge as shown in FIG. 8B. Further movement of the head 203 may result in further convergence as shown in FIG. 8C, until the lines 272, 274 become collinear as shown in FIG. 8D. At this point, the calibrated working distance is set. For reference, the calibrated working distance is represented in FIG. 7 by reference numeral 216 as the distance from the sensor portion 218 of the extensometer 201 to the face of the specimen. In reality, a distance from the specimen face 113 to any point on the housing 211/head 203 (e.g., to the front-most portion of the housing 211) may be used as a reference for the calibrated working distance as the sensor portion 218 is fixed relative to the housing/head.

The lasers 202, 204 are, during manufacture and assembly, adjusted to ensure the respective planes, 272, 274 intersect at the appropriate distance from the head 203 corresponding to the calibrated working distance. Once so positioned and aimed, further adjustment of the lasers 202, 204 is, at least in some embodiments, unnecessary by the end user.

When the lines converge as shown in FIG. 8D, the thumbwheel 210 may be tightened, effectively locking the head 203, and thus the extensometer 201, at the desired calibrated working distance 216 from the face 113 of the test specimen 112 (see FIG. 7). If multiple specimens of identical thickness are to be tested, the operator may move the stop 208 (see FIG. 4) until it abuts a front edge of the upper slide 213 (see FIG. 5) and then tighten the thumbwheel 209. As a result, the operator may be able to move the head 203 rearwardly when loading a new specimen, and then slide the head forwardly until it abuts the stop 208, at which point the thumbwheel 210 may be tightened again. That is to say, the stop 208 may allow the extensometer 201/head 203 to be quickly located for subsequent tests without necessitating the entire repositioning protocol via the lasers 202, 204 (though the lasers may still be energized to verify calibrated working distance).

Extensometer positioning systems in accordance with embodiments of the present disclosure may thus provide various benefits over known non-contact extensometers. For example, in addition to accurate, rapid, and repeatable extensometer positioning, systems like those described herein may increase testing throughput by, for example, resetting the extensometer automatically (e.g., automatically de-energizing the diffuse illuminator 214 and resetting the extensometer output) whenever the lasers 202, 204 are energized as may occur when a new specimen is inserted into the test machine. Further, positioning systems in accordance with embodiments of the present disclosure achieve extensometer ranging without, as described above, gauge blocks or other physical devices, and furthermore, without the use of potentially complex software metrics (e.g., sharpness, scaling, focus) otherwise known in the industry.

While systems and methods are shown and described herein above for accurately locating a non-contact extensometer relative to a test specimen, other applications are also contemplated. For example, the same or similar positioning systems may be used to ensure accurate initial positioning/alignment of a test specimen (e.g., specimen 112) within specimen grips (e.g., grips 110).

Figure 9A:
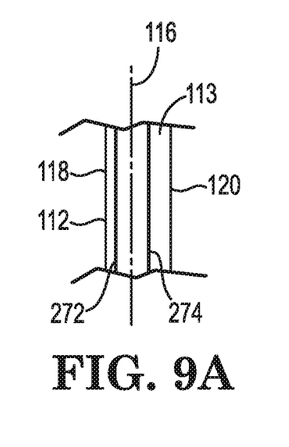
FIGS. 9A and 9B illustrate examples of when two laser lines indicate the test specimen is not centered on the test axis.
Figure 9B:
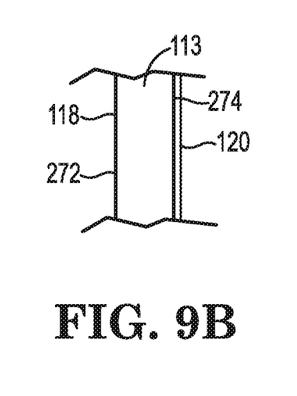
Figure 9C:
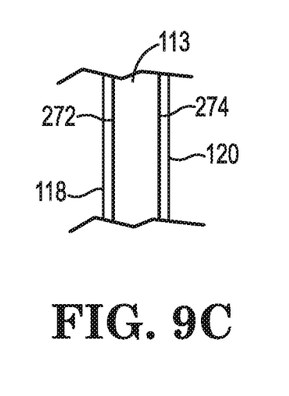
FIG. 9C illustrates a test specimen centered along the test axis.

To illustrate use of such positioning systems for specimen location, reference is made to FIGS. 9A-9D. As shown in FIG. 9A, after placement and clamping of specimen 112 within the grips 110 (not shown in FIGS. 9A-9D, but see FIGS. 1 and 2), the lasers 202, 204 may be energized to illuminate the planes/lines 272, 274 as already described herein. Upon illumination, the lines 272, 274 may appear asymmetrical on the specimen itself. That is, the two laser lines 272, 274 may not be centered upon the specimen face 113 as shown in FIG. 9A. It may be helpful in this instance to move the head 203 away from the specimen until one of the laser lines (e.g., line 272) aligns with a corresponding edge (e.g., first edge 118) of the specimen as shown in FIG. 9B. If the line 272 is aligned with the edge 118 and the line 274 is offset (in either direction) from the opposite second edge 120, then the specimen 112 is transversely shifted in the grips such that a centerline axis of the specimen is offset from the test axis 116. As eccentric loading of the specimen may adversely affect testing, the operator may re-mount the specimen to correct its position within the grips. FIG. 9C illustrates the lines 272, 274 once the specimen 112 is accurately centered within the grips 110 (again, it may be beneficial to move the head 203 until one of the lines 272, 274 is positioned at or very near its corresponding edge 118, 120 and then compare the proximity of the other line 272, 274 with its corresponding edge of the specimen).

Figure 9D:
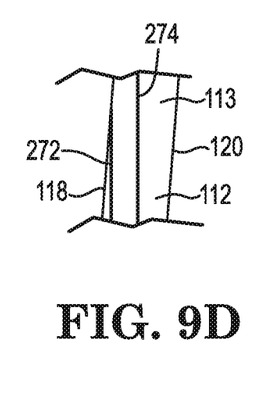
FIG. 9D illustrates exemplary laser line locations when the test specimen is canted or tilted relative to the test axis.

In addition to assisting with transverse centering of the specimen 112, positioning systems in accordance with embodiments of the present disclosure may also assist with ensuring the specimen is not canted or tilted within the grips. For instance, as shown in FIG. 9D, when one (or both) of the lasers lines 272, 274 is not visible along a length of the face 113 of the specimen 112 (e.g., the lines 272, 274 are not parallel to the sides 118, 120), the specimen is not aligned with the test axis. In such an instance, the operator may re-mount the specimen 112 and then re-verify its alignment relative to the test axis 116 as described herein above.

Accordingly, one of skill can appreciate that positioning systems in accordance with embodiments of the present disclosure may be used independent of any extensometer to assist with accurate specimen location and alignment within the test machine. Such specimen positioning systems may be generally identical to the system 200 described herein except that such "specimen-only" positioning systems may not include an extensometer as part of the head 203 (i.e., the head 203 may include generally only the lasers 202, 204). Alternatively, specimen positioning systems like those described herein could function using only a single pattern illuminator such as the laser 202 (e.g., an illuminator adapted to illuminate a single pattern such as a line or grid). However, in most other respects, the exemplary specimen positioning system may be similar to the extensometer positioning system 200 already described and is, therefore, not separately illustrated herein.

While such specimen-only positioning system could include a base and bearing as described herein, other embodiments may not require such robust mounting. For example, specimen positioning systems may not require the bearing and rail configuration at all and could, instead, utilize a more simplistic mounting. While such mounting may still benefit from movement toward and away (e.g., translation, pivoting) from the specimen, specimen positioning in accordance with embodiments of the present disclosure could also be achieved using a fixed mount (e.g., fixed to the test frame or base).

Figure 10A:
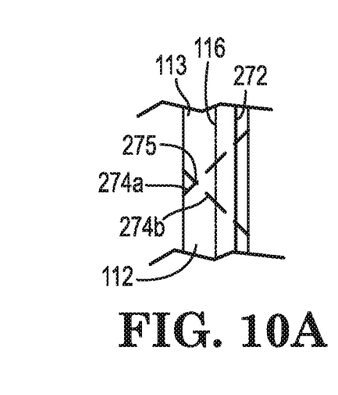
FIG. 10A illustrates the two patterns visible on a test specimen when a distance to specimen is more than (or less than) the calibrated working distance.
Figure 10B:
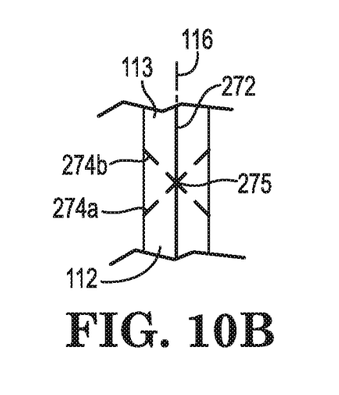
FIG. 10B is a similar view after movement of the sensor (or specimen) to a position corresponding to the calibrated working distance.

As illustrated in FIGS. 1-9D, positioning systems in accordance with embodiments of the present disclosure may use pattern illuminators that each illuminate a plane (e.g., appearing as a vertical line on the face of the specimen) parallel to the other. However, pattern illuminators that generate patterns other than single, parallel lines are also contemplated. For example, FIGS. 10A and 10B illustrate pattern illuminators that produce different patterns. In this particular embodiment, the first pattern illuminator (e.g., first laser 202) illuminates a vertical line or plane 272 as already described herein. However, the second pattern illuminator (e.g., laser 204) may illuminate a second pattern having two secondary lines 274a, 274b (collectively referred to herein as 274) intersecting one another at a crossing 275 to form an "X" shape (note that the lines 274 (274a, 274b) are shown as broken lines for illustration purposes only and would, in practice, form continuous visible lines on the face of the specimen). The head (or specimen) may then be moved as described herein until the first line 272 intersects the crossing 275 (the predetermined geometry), which again will occur when the head 203 is located at the calibrated working distance from the face 113 of the specimen as shown in FIG. 10B.

Using one pattern illuminator that illuminates two lines 274a, 274b as shown by the lines 274a, 274b in FIGS. 10A-10B may provide certain benefits. For instance, such illuminators may simplify manufacturing and calibration as it would no longer be necessary to control parallelism between two illuminated vertical lines (e.g., as may be required with the lines/planes 272, 274 shown in FIGS. 8A-8D).

Figure 11A:
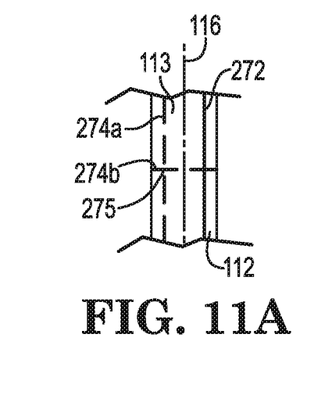
FIG. 11A illustrates the two patterns visible on a test specimen when a distance to specimen is more than (or less than) the calibrated working distance.
Figure 11B:
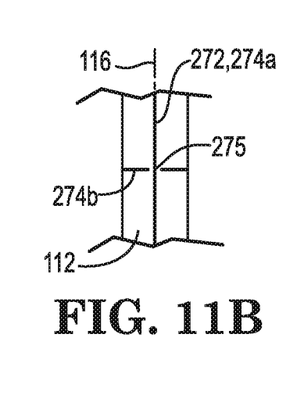
FIG. 11B is a similar view after movement of the sensor (or specimen) to a position corresponding to the calibrated working distance.

FIGS. 11A-11B illustrate a slight variation of the embodiment shown in FIGS. 10A-10B. In this configuration, the illuminator 204 may be adapted to again illuminate two lines 274a, 274b. However, this time the lines 274a, 274b may be configured as a cross or "+" shape as shown that intersect one another at a crossing 275. As with the embodiment of FIGS. 10A-10B, the head (or specimen) may be moved as described herein until the first line 272 intersects the crossing 275, which again will occur when the head 203 is located at the calibrated working distance from the face 113 of the specimen as shown in FIG. 11B.

Figure 12A:
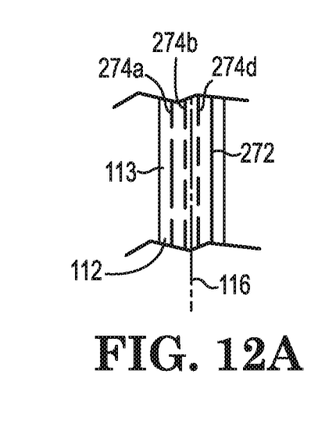
FIG. 12A illustrates the two patterns visible on a test specimen when a distance to specimen is more than (or less than) the calibrated working distance.
Figures 12B, 13A:
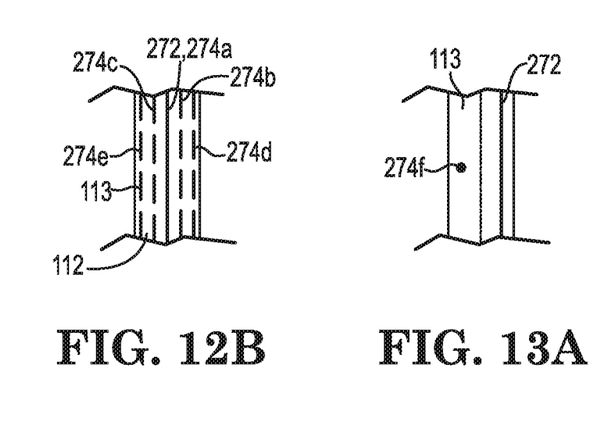
FIG. 12B is a similar view after movement of the sensor (or specimen) to a position corresponding to the calibrated working distance.
FIG. 13A illustrates the two patterns visible on a test specimen when a distance to specimen is more than (or less than) the calibrated working distance.

FIGS. 12A-12B illustrate still another illumination pattern in accordance with embodiments of the present disclosure. In this particular embodiment, the laser 202 may again illuminate a first line or plane 272 as shown, while the laser 204 may illuminate multiple parallel lines 274a, 274b, 274c, 274d, and 274e (274c and 274e shown in FIG. 12B only). In this particular embodiment, the head 203 may be moved until the line 274a intersects the line 272 in a predetermined geometry (e.g., they become collinear). The lines 274b, 274c, 274d, and 274e may then be used, for example, as a gage to indicate whether the specimen is centered appropriately relative to the axis 116 (by observing the symmetry of the lines 274b-274e upon the face 113 of the specimen 112).

Figure 13B:
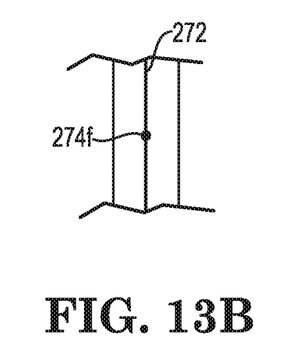
FIG. 13B is a similar view after movement of the sensor (or specimen) to a position corresponding to the calibrated working distance.

While illuminated lines provide various benefits as described herein, other embodiments may permit accurate positioning using other illuminated patterns altogether. For example, FIGS. 13A-13B illustrate a positioning system using a first illuminated pattern (e.g., from the laser 202) forming a line 272 in a manner already described herein. However, the second illuminated pattern (e.g., from the laser 204) may be a discrete point 274f on the specimen face 113. As the head (or specimen) is moved as described herein, the first line 272 may eventually reach the calibrated working distance, wherein the line 272 intersects or overlays the point 274f as shown in FIG. 13B. Again, this intersection corresponds to the head 203 being located at the calibrated working distance from the face 113 of the specimen.

Illustrative embodiments are described and reference has been made to possible variations of the same. These and other variations, combinations, and modifications will be apparent to those skilled in the art, and it should be understood that the claims are not limited to the illustrative embodiments set forth herein.

What is claimed is:

1. A positioning system for use with locating components within a materials test frame, the system comprising:
    a base positionable relative to the test frame;
    a head connected to the base and movable toward and away from a test specimen secured within the test frame;
    an extensometer supported by the head, the extensometer comprising at least one sensor for measuring deformation of the test specimen;
    a first pattern illuminator connected to the head and adapted to illuminate a visible first pattern on the test specimen; and
    a second pattern illuminator connected to the head and adapted to illuminate a visible second pattern on the test specimen, wherein the first and second patterns intersect one another in a predetermined geometry when the extensometer is located at a calibrated working distance from the test specimen, and do not intersect one another in the predetermined geometry when the extensometer is at a distance different than the calibrated working distance.

2. The positioning system of claim 1, wherein the first and second patterns comprise first and second lines, respectively, that are parallel to, and offset from, one another when the extensometer is located at a distance different than the calibrated working distance, and are collinear when the extensometer is located at the calibrated working distance.

3. The positioning system of claim 2, wherein the first and second lines are parallel to a test axis of the test frame.

4. The positioning system of claim 2, wherein the second pattern comprises a plurality of parallel lines.

5. The positioning system of claim 3, wherein the first and second lines are vertical.

6. The positioning system of claim 1, wherein the first pattern comprises a first line, and the second pattern comprises two secondary lines intersecting one another at a crossing, wherein the first line intersects the crossing when the head extensometer is located at the calibrated working distance.

7. The positioning system of claim 6, wherein the first line is parallel with a test axis of the test frame.

8. The positioning system of claim 1, wherein the first pattern comprises a first line, and the second pattern comprises a point, wherein the point overlays the first line when the extensometer is located at the calibrated working distance.

9. The positioning system of claim 8, wherein the first line is parallel with a test axis of the test frame.

10. The positioning system of claim 1, wherein the base comprises a mount adapted to attach to the test frame, and a support pivotally attached to the mount.

11. The positioning system of claim 10, wherein the head selectively translates relative to the support.

12. A positioning system for locating a non-contact extensometer relative to a test specimen secured within a specimen area, and along a test axis, of a test frame, the system comprising:
   a base adapted to attach to the test frame;
   a head connected to the base and supporting the non-contact extensometer, the extensometer comprising at least one sensor for measuring deformation of the test specimen;
   a first pattern illuminator connected to the head and adapted to illuminate a first pattern obliquely intersecting the test specimen; and
   a second pattern illuminator connected to the head and adapted to illuminate a second pattern also obliquely intersecting the test specimen, wherein the first and second patterns: intersect one another in a predetermined geometry on a face of the test specimen when the non-contact extensometer is located at a calibrated working distance from the test specimen; and do not intersect one another in the predetermined geometry when the non-contact extensometer is located at a distance different than the calibrated working distance.

13. The positioning system of claim 12, wherein the first and second patterns each comprise at least one line.

14. The positioning system of claim 12, wherein one of the first and second patterns comprises two lines intersecting one another at a crossing.

15. The positioning system of claim 12, wherein one of the first and second patterns comprises a discrete point.

16. The positioning system of claim 12, wherein the base comprises a linear bearing supporting the head, the linear bearing adapted to allow translational movement of the head in a direction extending radially to the test axis of the test frame.

17. The positioning system of claim 16, wherein the linear bearing comprises a stop adapted to limit translation of the head towards the specimen.

18. The positioning system of claim 16, wherein the linear bearing comprises a lock adapted to lock the head relative to the linear bearing.

19. The positioning system of claim 16, wherein the base comprises a mount adapted to pivotally support the linear bearing.

20. A method for positioning a sensor relative to a face of a test specimen, the method comprising:
   aligning the sensor with the test specimen, the sensor adapted to measure deformation of the test specimen;
   activating two pattern illuminators associated with the sensor, the two pattern illuminators illuminating two patterns upon the face of the test specimen; and
   changing a distance between the sensor and the test specimen until the two patterns align on the face of the test specimen in a predetermined geometry indicating that the sensor is located at a calibrated working distance from the test specimen.

21. The method of claim 20, wherein changing the distance between the sensor and the test specimen comprises moving the sensor toward or away from the test specimen.

22. The method of claim 21, wherein moving the sensor toward or away from the test specimen comprises sliding the sensor along a linear bearing.

23. The method of claim 20, wherein activating the two pattern illuminators comprises illuminating a first pattern with a first laser and a second pattern with a second laser, wherein the first pattern and the second pattern each obliquely intersect the face of the test specimen.

24. The method of claim 20, wherein the two patterns each comprise a line parallel to the other.

25. The method of claim 20, wherein the two patterns each comprise a vertical line.

26. The method of claim 25, further comprising using the two patterns to center the test specimen within a test frame.

27. The method of claim 25, further comprising using the first and second patterns to align the specimen within a test frame.

* * * * *